(12) United States Patent
Medoff

(10) Patent No.: US 8,980,601 B2
(45) Date of Patent: *Mar. 17, 2015

(54) MARKING PAPER PRODUCTS

(71) Applicant: Xyleco, Inc., Woburn, MA (US)

(72) Inventor: Marshall Medoff, Brookline, MA (US)

(73) Assignee: Xyleco, Inc., Woburn, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/308,223

(22) Filed: Jun. 18, 2014

(65) Prior Publication Data

US 2014/0304863 A1    Oct. 9, 2014

Related U.S. Application Data

(63) Continuation of application No. 13/440,141, filed on Apr. 5, 2012, which is a continuation of application No. PCT/US2010/052388, filed on Oct. 12, 2010.

(60) Provisional application No. 61/251,633, filed on Oct. 14, 2009.

(51) Int. Cl.
| | |
|---|---|
| G06K 5/00 | (2006.01) |
| D21H 21/48 | (2006.01) |
| D21H 25/04 | (2006.01) |
| G03C 11/02 | (2006.01) |
| G21K 5/00 | (2006.01) |
| G01N 33/34 | (2006.01) |
| C12M 1/00 | (2006.01) |
| H01J 3/02 | (2006.01) |
| H01J 3/04 | (2006.01) |

(52) U.S. Cl.
CPC .................. *G06K 5/00* (2013.01); *C12M 45/06* (2013.01); *C12M 45/00* (2013.01); *H01J 3/02* (2013.01); *H01J 3/04* (2013.01); *D21H 21/48* (2013.01); *D21H 25/04* (2013.01); *G03C 11/02* (2013.01); *G21K 5/00* (2013.01); *G01N 33/346* (2013.01)
USPC ...................................................... 435/174

(58) Field of Classification Search
None
See application file for complete search history.

(56) References Cited

U.S. PATENT DOCUMENTS

| | | | |
|---|---|---|---|
| 3,962,054 A | 6/1976 | Wattiez et al. | |
| 4,138,522 A | 2/1979 | Ishizuka et al. | |
| 4,248,500 A | 2/1981 | Pernicano et al. | |
| 4,486,585 A | 12/1984 | Turnunen et al. | |
| 6,264,791 B1 | 7/2001 | Sun et al. | |
| 6,638,579 B2 | 10/2003 | Ross et al. | |
| 6,872,927 B2 | 3/2005 | Geisler et al. | |
| 6,958,108 B1 | 10/2005 | Vuorinen | |
| 7,867,358 B2 * | 1/2011 | Medoff | 162/50 |
| 8,052,838 B2 | 11/2011 | Medoff | |
| 2006/0169427 A1 | 8/2006 | Cartier | |
| 2009/0117353 A1 | 5/2009 | Stubbs et al. | |
| 2009/0283229 A1 | 11/2009 | Medoff | |
| 2010/0206501 A1 | 8/2010 | Medoff | |
| 2010/0297720 A1 | 11/2010 | Medoff et al. | |
| 2010/0304440 A1 | 12/2010 | Medoff | |
| 2011/0081335 A1 | 4/2011 | Medoff | |
| 2011/0081336 A1 | 4/2011 | Medoff | |
| 2011/0111456 A1 | 5/2011 | Medoff | |
| 2011/0139383 A1 | 6/2011 | Medoff | |
| 2012/0003704 A1 | 1/2012 | Medoff | |
| 2012/0285639 A1 | 11/2012 | Medoff | |

FOREIGN PATENT DOCUMENTS

| | | |
|---|---|---|
| EP | 1215216 | 6/2002 |
| JP | 3-008898 | 1/1991 |
| WO | 2008143002 | 11/2008 |
| WO | WO 2009/134746 | 11/2009 |
| WO | WO 2009/134764 | 11/2009 |

OTHER PUBLICATIONS

Bouchard J., et al., "The Effects of Ionizing Radiation on the Cellulose of Woodfree Paper" Cellulose, (2006), vol. 13, pp. 601-610.
Adamo, M. and Magaudda, G. "Susceptibility of Printed Paper to Attack of Chewing Insects After Gamma Irradiation and Ageing", 2002, url:www.viks.sk/chk/res_2_03_95_105.doc, 2002, retrieved Jun. 12, 2013, 8 pages.
Ferrero, F.; Testore, F; Tonin, C; Innocenti, R., "Surface Degradation of Linen Textiles Induced by Laser Treatment: Comparison with Electron Beam and Heat Source" AUTEX Res. J., Sep. 2002 2(3), pp. 109-114.
Whatman "Protran Nitrocellulose Membranes" Proteomics and Glycomics Brochure, TOPAS-BS, 2004, 6 pages.
Stevens, Malcolm P., "Evaluation, Characterization, and Analysis of Polymers" Polymer Chemistry: An Introduction, 3rd Ed., 1999, Chapter 5, pp. 129-166.
Fahey, Mary, "The Care and Preservation of Archival Materials" The Henry Ford—URL: http://www.thehenryford.org/research/caring/materials.aspx, 2000, accessed online Dec. 5, 2012, 6 pages.

* cited by examiner

*Primary Examiner* — Jon P Weber
*Assistant Examiner* — Aaron J Kosar
(74) *Attorney, Agent, or Firm* — Leber Patent Law P.C.

(57) ABSTRACT

Methods of marking paper products and marked paper products are provided. Some methods include irradiating the paper product to alter the functionalization of the paper.

11 Claims, 4 Drawing Sheets

MARKING PAPER PRODUCTS

RELATED APPLICATIONS

This application is a continuation U.S. Ser. No. 13/440,141, filed Apr. 5, 2012, which is a continuation of International Serial No. PCT/US2010/052388, filed Oct. 12, 2010, which claims priority of U.S. Provisional Application Ser. No. 61/251,633, filed on Oct. 14, 2009. The entirety of each of these applications is incorporated herein by reference.

TECHNICAL FIELD

This invention relates to methods and systems for marking paper products, such as currency, and products produced by such methods and systems.

BACKGROUND

Paper, as that term is used herein, refers to the wide variety of cellulose-based sheet materials used for writing, printing, packaging, and other applications. Paper may be used, for example, but without limitation, in the following applications: as paper money, bank notes, stock and bond certificates, checks, postage stamps, and the like; in books, magazines, newspapers, and art; for packaging, e.g., paper board, corrugated cardboard, paper bags, envelopes, wrapping tissue, boxes; in household products such as toilet paper, tissues, paper towels and paper napkins; paper honeycomb, used as a core material in composite materials; building materials; construction paper; disposable clothing; and in various industrial uses including emery paper, sandpaper, blotting paper, litmus paper, universal indicator paper, paper chromatography, battery separators, and capacitor dielectrics.

In some applications, for example when paper is used as currency and in other financial applications, it is often desirable to be able to "mark" or "tag" the paper with a special marking that is not visible to the naked eye, and/or cannot easily be produced by counterfeiters. Marking can be used, for example, to prevent or detect counterfeiting of currency, art and other valuable documents. Marking can also be used on currency to allow the currency to be traced and/or identified, e.g., if it is stolen or used in a criminal transaction.

SUMMARY

The invention is based, in part, on the discovery that by irradiating paper at appropriate levels, the functionalization of the irradiated paper can be altered, thereby making the paper distinguishable, e.g., by infrared spectrometry (IR) or other techniques, from paper that has not been irradiated. In some cases, the paper is also distinguishable from paper that has been irradiated, but under other process conditions. As a result, paper products such as currency can be "marked" by the methods described herein. In some implementations, the marking is invisible to the naked eye, e.g., it is detected by the use of instruments. In other implementations, the marking is visible to the naked eye. Generally, the marking is difficult to replicate without relatively sophisticated equipment, thereby making counterfeiting more difficult.

By "functionalization," we mean the functional groups that are present on or within the paper.

In one aspect, the invention features methods of making a marked paper product. Some methods include irradiating a paper product under conditions selected to alter the functionalization of at least an area of the paper product.

Some implementations include one or more of the following features. The paper can be irradiated with ionizing radiation. The dose of ionizing radiation can be at least, for example, 0.10 MRad, e.g., at least 0.25 MRad. The dose of ionizing radiation can be controlled to a level of about 0.25 to about 5 MRad. Irradiating can include irradiating with gamma radiation, and/or with electron beam radiation or other particles. Electrons in the electron beam can have an energy of at least 0.25 MeV, e.g., from about 0.25 MeV to about 7.5 MeV.

The methods can further include quenching the irradiated paper product. For example, quenching can be performed in the presence of a gas selected to react with radicals present in the irradiated paper product.

In some cases, only a portion of the paper product is irradiated. In some cases, only a portion of the irradiated area, or only a portion of the paper product as a whole, is quenched. For example, an area that is to remain unmarked and/or unquenched can be masked.

Irradiation can occur during formation of the paper product. Formation can include amalgamating the pulp material into a wet paper web. Irradiating can be performed on the wet paper web or prior to formation of the wet paper web. Formation can further include drying the wet paper web, and irradiating can occur after drying. In some implementations, powders, granulates, chemical solutions, dyes, inks, or gases can be applied, singularly or in combination, before, during, or after formation of the paper.

In another aspect, the invention features marked paper products that include a cellulosic or lignocellulosic fibrous material containing functional groups not present in a naturally occurring cellulosic or lignocellulosic fibrous material from which the marked paper product was obtained.

The cellulosic or lignocellulosic material in the paper product can be selected, for example, from the group consisting of fiber derived from wood and recycled paper, vegetable fiber materials, such as cotton, hemp, linen, rice, sugarcane, bagasse, straw, bamboo, kenaf, jute, and flax, and mixtures thereof. In some embodiments metal or inorganic fibers can also be included with the cellulosic or lignocellulosic material or included in a portion of the paper product being irradiated.

In a further aspect, the invention features a method of identifying whether a paper product is marked. The method includes comparing the functionalization of a sample paper product to the functionalization of a marked paper product.

In some cases, the method includes determining the functionalization of the sample paper product using infrared spectrometry (IR). The method may include comparing the number of carboxylic acid groups present in the sample paper product with the number of carboxylic acid groups present in the marked paper product.

In some cases, the functionalization is determined using atomic force microscopy (AFM), chemical force microscopy (CFM), or electron spin resonance (ESR).

The paper product may be, for example, currency or a work of art.

In any of the methods disclosed herein, functionalization can include increasing the number of carboxylic acid groups present in the paper. The number of carboxylic acid groups is determined by titration.

The irradiated material can also include functional groups selected from the group consisting of aldehyde groups, nitroso groups, nitrile groups, nitro groups, ketone groups, amino groups, alkyl amino groups, alkyl groups, chloroalkyl groups, chlorofluoroalkyl groups, and enol groups. In some implementations, the irradiated material may include a plurality of saccharide units arranged in a molecular chain, and from about 1 out of every 5 to about 1 out of every 1500 saccharide units comprises a nitroso, nitro, or nitrile group, e.g., from about 1 out of every 10 to about 1 out of every 1000 saccharide units of each chain comprises a nitroso, nitro, or nitrile group, or from about 1 out of every 35 to about 1 out of every 750 saccharide units of each chain comprises a nitroso, nitro, or nitrile group. In some cases the irradiated material comprises a mixture of nitrile groups and carboxylic acid groups.

In some embodiments, the saccharide units can include substantially only a single type of group, such as a carboxylic acid group, a nitrile group, a nitroso group or a nitro group.

The term "paper," as used herein, is intended to include cellulose-containing sheet materials and composite sheet materials containing cellulose. For example, the paper may include cellulose in a plastic matrix, or cellulose combined with additives or binders.

In any of the methods disclosed herein, radiation may be applied from a device that is in a vault.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All mentioned publications, patent applications, patents, and other references are incorporated herein by reference in their entirety. In case of conflict, the present specification, including definitions, will control. In addition, the materials, methods and examples are illustrative only and not intended to be limiting.

Other features and advantages of the invention will be apparent from the following detailed description, and from the claims.

DETAILED DESCRIPTION

As discussed above, the invention is based, in part, on the discovery that by irradiating fibrous materials, i.e., cellulosic and lignocellulosic materials, at appropriate levels, the molecular structure of at least a cellulosic portion of the fibrous material can be changed, changing the functionalization of the fibrous material. In addition to marking the paper, changing the functionalization can also favorably affect the surface properties of a paper product, e.g., the receptivity of the surface to coatings, inks and dyes.

Moreover, the change in molecular structure can include a change in any one or more of an average molecular weight, average crystallinity, surface area, polymerization, porosity, branching, grafting, and domain size of the cellulosic portion. These changes in molecular structure can in turn result in favorable alterations of the physical characteristics exhibited by the fibrous materials. Such changes are discussed in detail in U.S. Ser. No. 12/417,707, filed Apr. 3, 2009, the full disclosure of which is incorporated herein by reference.

Radiation can be applied at one or more selected stages of the papermaking process. In some cases, irradiation will improve the strength and tear resistance of the paper, by increasing the strength of the cellulosic fibers of which the paper is made. In addition, treating the cellulosic material with radiation can sterilize the material, which may reduce the tendency of the paper to promote the growth of mold, mildew of the like. Irradiation is generally performed in a controlled and predetermined manner to provide optimal properties for a particular application, by selecting the type or types of radiation employed and/or dose or doses of radiation applied.

Figure 1:
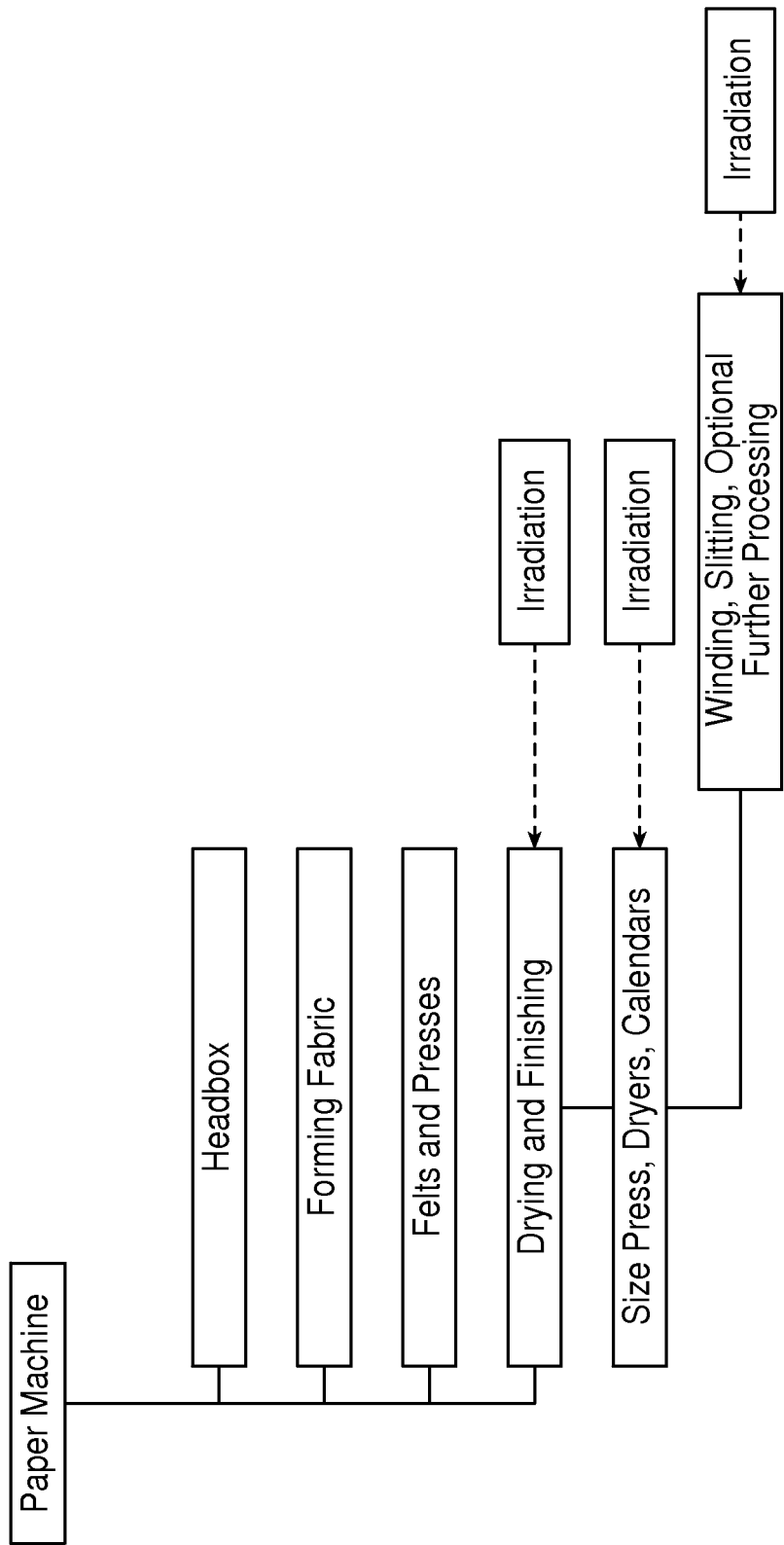
FIG. 1 is a diagrammatic view of a paper making system.

A low dose of ionizing radiation can be applied, for example, after pulping and before amalgamation of the pulped fibers into a web; to the wet fiber web; to the paper web during or after drying; or to the dried paper web, e.g., before, during, or after subsequent processing steps such as sizing, coating, and calendering. It is generally preferred that radiation be applied to the web when it has a relatively low moisture content. In the example shown in FIG. 1, irradiation can be performed during drying and finishing, e.g., between sizing, drying, pressing and calendaring operations, or during post-processing, e.g., to the finished paper in roll, slit roll or sheet form.

As noted above, in some embodiments radiation is applied at more than one point during the manufacturing process. For example, ionizing radiation can be used at a relatively high dose to form or to help form the pulp, and then later at a relatively lower dose to alter the functionalization of the paper. If desired, high dose radiation can be applied to the finished paper at selected areas of the paper web to create locally weakened areas, e.g., to provide tear zones.

As a practical matter, using existing technology, it is generally most desirable to integrate the irradiation step into the papermaking process either after pulping and prior to introduction of the pulp to the papermaking machine, after the web has exited the papermaking machine, typically after drying and sizing, or during or after processing of the web into a final product. In some cases, a finished or existing paper product, such as currency, art or documents, can be irradiated to mark the product. However, as noted above, irradiation may be performed at any desired stage in the process.

Irradiating to Affect Material Functional Groups

After treatment with one or more ionizing radiations, such as photonic radiation (e.g., X-rays or gamma-rays), e-beam radiation or irradiation with particles heavier than electrons that are positively or negatively charged (e.g., protons or carbon ions), the paper becomes ionized; that is, the paper includes radicals at levels that are detectable, for example, with an electron spin resonance spectrometer. After ionization, the paper can be quenched to reduce the level of radicals in the ionized material, e.g., such that the radicals are no longer detectable with the electron spin resonance spectrometer. For example, the radicals can be quenched by the application of sufficient pressure to the ionized material and/or by contacting the ionized material with a fluid, such as a gas or liquid, that reacts with (quenches) the radicals. Various gases, for example nitrogen or oxygen, or liquids, can be used to at least aid in the quenching of the radicals and to functionalize the ionized material with desired functional groups. Thus, irradiation followed by quenching can be used to provide pulp or paper with desired functional groups, including, for example, one or more of the following: aldehyde groups, enol groups, nitroso groups, nitrile groups, nitro groups, ketone groups, amino groups, alkyl amino groups, alkyl groups, chloroalkyl groups, chlorofluoroalkyl groups, and/or carboxylic acid groups. These groups increase the hydrophilicity of the region of the material where they are present. In some implementations, the paper web is irradiated and quenched, before or after processing steps such as coating and calendering, to affect the functionality within and/or at the surface of the paper and thereby affect the ink receptivity and other properties of the paper.

Figure 2:
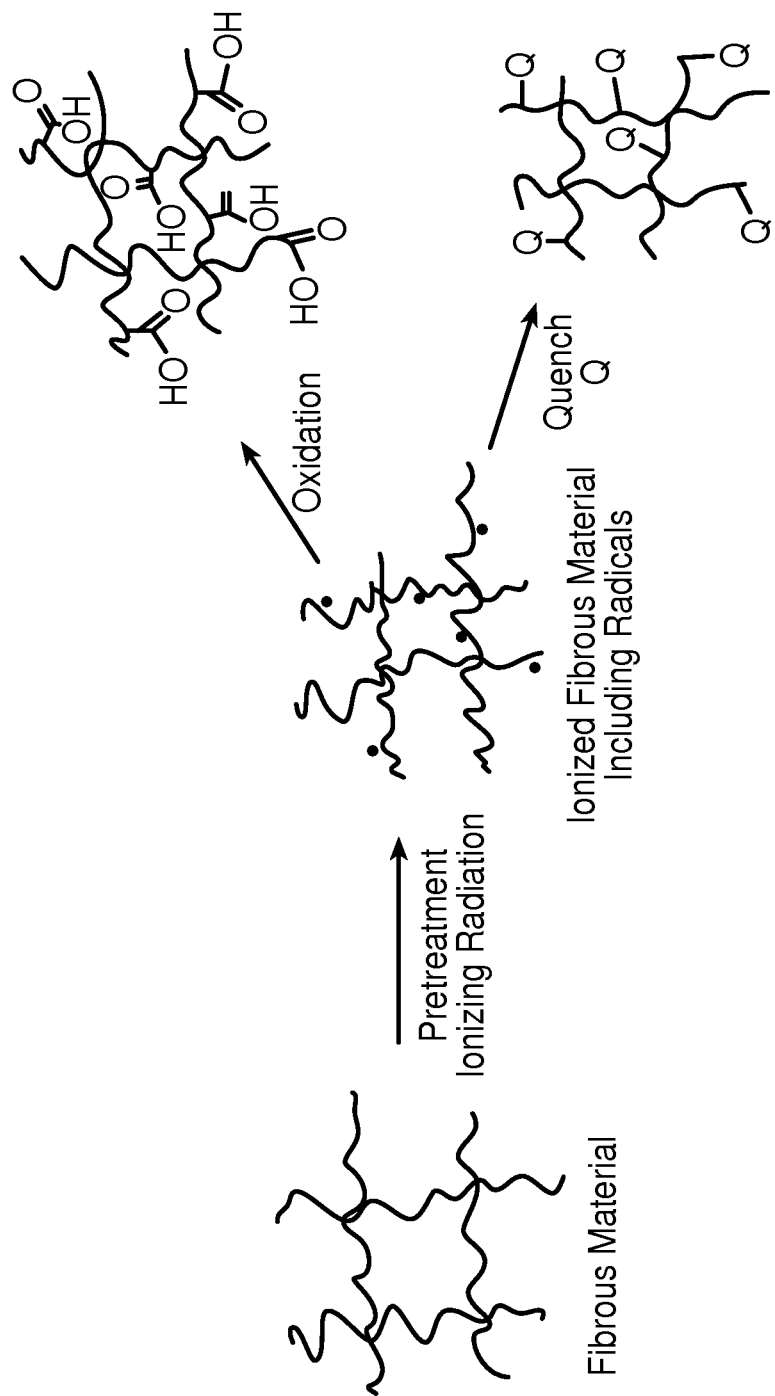
FIG. 2 is a diagram that illustrates changing a molecular and/or a supramolecular structure of a fibrous material.

FIG. 2 illustrates changing a molecular and/or a supramolecular structure of fibrous material, such as paper feedstock, paper precursor (e.g., a wet paper web), or paper, by pretreating the fibrous material with ionizing radiation, such as with electrons or ions of sufficient energy to ionize the material, to provide a first level of radicals. As shown in FIG. 2, if the ionized material remains in the atmosphere, it will be oxidized, e.g., to an extent that carboxylic acid groups are generated by reaction with the atmospheric oxygen. Since the radicals can "live" for some time after irradiation, e.g., longer than 1 day, 5 days, 30 days, 3 months, 6 months, or even longer than 1 year, material properties can continue to change over time, which in some instances can be undesirable.

Detecting radicals in irradiated samples by electron spin resonance spectroscopy and radical lifetimes in such samples is discussed in Bartolotta et al., Physics in Medicine and Biology, 46 (2001), 461-471 and in Bartolotta et al., Radiation Protection Dosimetry, Vol. 84, Nos. 1-4, pp. 293-296 (1999). As shown in FIG. 2, the ionized material can be quenched to functionalize and/or to stabilize the ionized material.

In some embodiments, quenching includes application of pressure to the ionized material, such as by mechanically deforming the material, e.g., directly mechanically compressing the material in one, two, or three dimensions, or applying pressure to fluid in which the material is immersed, e.g., isostatic pressing. Pressure may be applied, e.g., by passing the paper through a nip. In such instances, the deformation of the material itself brings radicals, which are often trapped in crystalline domains, into proximity close enough for the radicals to recombine, or react with another group. In some instances, pressure is applied together with application of heat, e.g. a quantity of heat sufficient to elevate the temperature of the material to above a melting point or softening point of a component of the ionized material, such as lignin, cellulose or hemicellulose. Heat can improve molecular mobility in the material, which can aid in quenching of radicals. When pressure is utilized to quench, the pressure can be greater than about 1000 psi, such as greater than about 1250 psi, 1450 psi, 3625 psi, 5075 psi, 7250 psi, 10000 psi, or even greater than 15000 psi.

In some embodiments, quenching includes contacting the ionized material with fluid, such as liquid or gas, e.g., a gas capable of reacting with the radicals, such as acetylene or a mixture of acetylene in nitrogen, ethylene, chlorinated ethylenes or chlorofluoroethylenes, propylene or mixtures of these gases. In other particular embodiments, quenching includes contacting the ionized material with liquid, e.g., a liquid soluble in, or at least capable of penetrating into, the ionized material and reacting with the radicals, such as a diene, such as 1,5-cyclooctadiene. In some specific embodiments, the quenching includes contacting the ionized material with an antioxidant, such as Vitamin E. If desired, the material can include an antioxidant dispersed therein, and quenching can come from contacting the antioxidant dispersed in the material with the radicals.

Other methods for quenching are possible. For example, any method for quenching radicals in polymeric materials described in Muratoglu et al., U.S. Patent Publication No. 2008/0067724 and Muratoglu et al., U.S. Pat. No. 7,166,650, the disclosures of which are incorporated herein by reference in their entireties, can be utilized for quenching any ionized material described herein. Furthermore, any quenching agent (described as a "sensitizing agent" in the above-noted Muratoglu disclosures) and/or any antioxidant described in either Muratoglu reference, can be utilized to quench any ionized material.

Functionalization can be enhanced by utilizing heavy charged ions. For example, if it is desired to enhance oxidation, charged oxygen ions can be utilized for the irradiation. If nitrogen functional groups are desired, nitrogen ions or any ion that includes nitrogen can be utilized. Likewise, if sulfur or phosphorus groups are desired, sulfur or phosphorus ions can be used in the irradiation.

In some embodiments, after quenching, the quenched material can treated with one or more further doses of radiation, such as ionizing or non-ionizing radiation, and/or can be oxidized for additional molecular and/or supramolecular structure change.

In some embodiments, the fibrous material is irradiated under a blanket of inert gas, e.g., helium or argon, prior to quenching.

The location of the functional groups can be controlled, e.g., by selecting a particular type and dose of ionizing particles. For example, gamma radiation tends to affect the functionality of molecules within paper, while electron beam radiation tends to preferentially affect the functionality of molecules at the surface.

In some cases, functionalization of the material can occur simultaneously with irradiation, rather than as a result of a separate quenching step. In this case, the type of functional groups and degree of oxidation can be affected in various ways, for example by controlling the gas blanketing the material to be irradiated, through which the irradiating beam passes. Suitable gases include nitrogen, oxygen, air, ozone, nitrogen dioxide, sulfur dioxide and chlorine.

In some embodiments, functionalization results in formation of enol groups in the fibrous material. When the fibrous material is paper, this can enhance receptivity of the paper to inks, adhesives, coatings, and the like, and can provide grafting sites. Enol groups can help break down molecular weight, especially in the presence of added base or acid. Thus, the presence of such groups can assist with pulping. In the finished paper product, generally the pH is close enough to neutral that these groups will not cause a deleterious decrease in molecular weight.

Masking

In some cases it may be desirable to irradiate and/or quench only a small area of a paper product, e.g., to create a "watermark" or to irradiate a particular symbol printed on the paper, e.g., an "E" on currency. In such cases, the remainder of the paper product, which is to remain unmarked, can be masked.

If only a small portion is to be irradiated, the remainder is masked with a radioopaque material, e.g., lead or other heavy metal. The mask should be of sufficient thickness to prevent radiation from passing through, or to reduce the radiation that passes through sufficiently to prevent marking. If it is desired to mark a particular symbol, such as the E on currency, the paper product should be in registration with the mask such that the symbol to be marked is lined up with an opening in the mask. Techniques for such masking are well known, e.g., in the semiconductor industry.

If only a small portion is to be quenched, the remainder of the paper product can be masked during quenching, e.g., with a material that inhibits contact of the paper product with the liquid or gas used in quenching.

Particle Beam Exposure in Fluids

In some cases, the paper, or its cellulosic or lignocellulosic starting materials, can be exposed to a particle beam in the presence of one or more additional fluids (e.g., gases and/or liquids). Exposure of a material to a particle beam in the presence of one or more additional fluids can increase the efficiency of the treatment.

In some embodiments, the material is exposed to a particle beam in the presence of a fluid such as air. For example, particles accelerated in an accelerator can be coupled out of the accelerator via an output port (e.g., a thin membrane such as a metal foil), pass through a volume of space occupied by the fluid, and then be incident on the material. In addition to directly treating the material, some of the particles generate additional chemical species by interacting with fluid particles (e.g., ions and/or radicals generated from various constituents of air, such as ozone and oxides of nitrogen). These generated chemical species can also interact with the material. For example, any oxidant produced can oxidize the material.

In certain embodiments, additional fluids can be selectively introduced into the path of a particle beam before the beam is incident on the material. As discussed above, reactions between the particles of the beam and the particles of the introduced fluids can generate additional chemical species, which react with the material and can assist in functionalizing the material, and/or otherwise selectively altering certain properties of the material. The one or more additional fluids can be directed into the path of the beam from a supply tube, for example. The direction and flow rate of the fluid(s) that is/are introduced can be selected according to a desired exposure rate and/or direction to control the efficiency of the overall treatment, including effects that result from both particle-based treatment and effects that are due to the interaction of dynamically generated species from the introduced fluid with the material. In addition to air, exemplary fluids that can be introduced into the ion beam include oxygen, nitrogen, one or more noble gases, one or more halogens, and hydrogen.

Cooling Irradiated Materials

During treatment of the materials discussed above with ionizing radiation, especially at high dose rates, such as at rates greater then 0.15 Mrad per second, e.g., 0.25 Mrad/s, 0.35 Mrad/s, 0.5 Mrad/s, 0.75 Mrad/s or even greater than 1 Mrad/sec, the materials can retain significant quantities of heat so that the temperature of the material becomes elevated. While higher temperatures can, in some embodiments, be advantageous, e.g., when a faster reaction rate is desired, it is advantageous to control the heating to retain control over the chemical reactions initiated by the ionizing radiation, such as crosslinking and/or grafting.

For example, in one method, the material is irradiated at a first temperature with ionizing radiation, such as photons, electrons or ions (e.g., singularly or multiply charged cations or anions), for a sufficient time and/or a sufficient dose to elevate the material to a second temperature higher than the first temperature. The irradiated material is then cooled to a third temperature below the second temperature. If desired, the cooled material can be treated one or more times with radiation, e.g., with ionizing radiation. If desired, cooling can be applied to the material after and/or during each radiation treatment.

Cooling can in some cases include contacting the material with a fluid, such as a gas, at a temperature below the first or second temperature, such as gaseous nitrogen at or about 77 K. Even water, such as water at a temperature below nominal room temperature (e.g., 25 degrees Celsius) can be utilized in some implementations.

Types of Radiation

The radiation can be provided, e.g., by: 1) heavy charged particles, such as alpha particles; 2) electrons, produced, for example, in beta decay or electron beam accelerators; or 3) electromagnetic radiation, e.g., gamma rays, x-rays or ultraviolet rays. Different forms of radiation ionize the cellulosic or lignocellulosic material via particular interactions, as determined by the energy of the radiation.

Heavy charged particles include alpha particles, which are identical to the nucleus of a helium atom and are produced by alpha decay of various radioactive nuclei, such as isotopes of bismuth, polonium, astatine, radon, francium, radium, several actinides, such as actinium, thorium, uranium, neptunium, curium, californium, americium and plutonium.

Electrons interact via Coulomb scattering and bremsstrahlung radiation produced by changes in the velocity of electrons. Electrons can be produced by radioactive nuclei that undergo beta decay, such as isotopes of iodine, cesium, technetium and iridium. Alternatively, an electron gun can be used as an electron source via thermionic emission.

Electromagnetic radiation interacts via three processes: photoelectric absorption, Compton scattering and pair production. The dominating interaction is determined by the energy of incident radiation and the atomic number of the material. The summation of interactions contributing to the absorbed radiation in cellulosic material can be expressed by the mass absorption coefficient.

Electromagnetic radiation is subclassified as gamma rays, x-rays, ultraviolet rays, infrared rays, microwaves or radio waves, depending on its wavelength.

Figure 3:
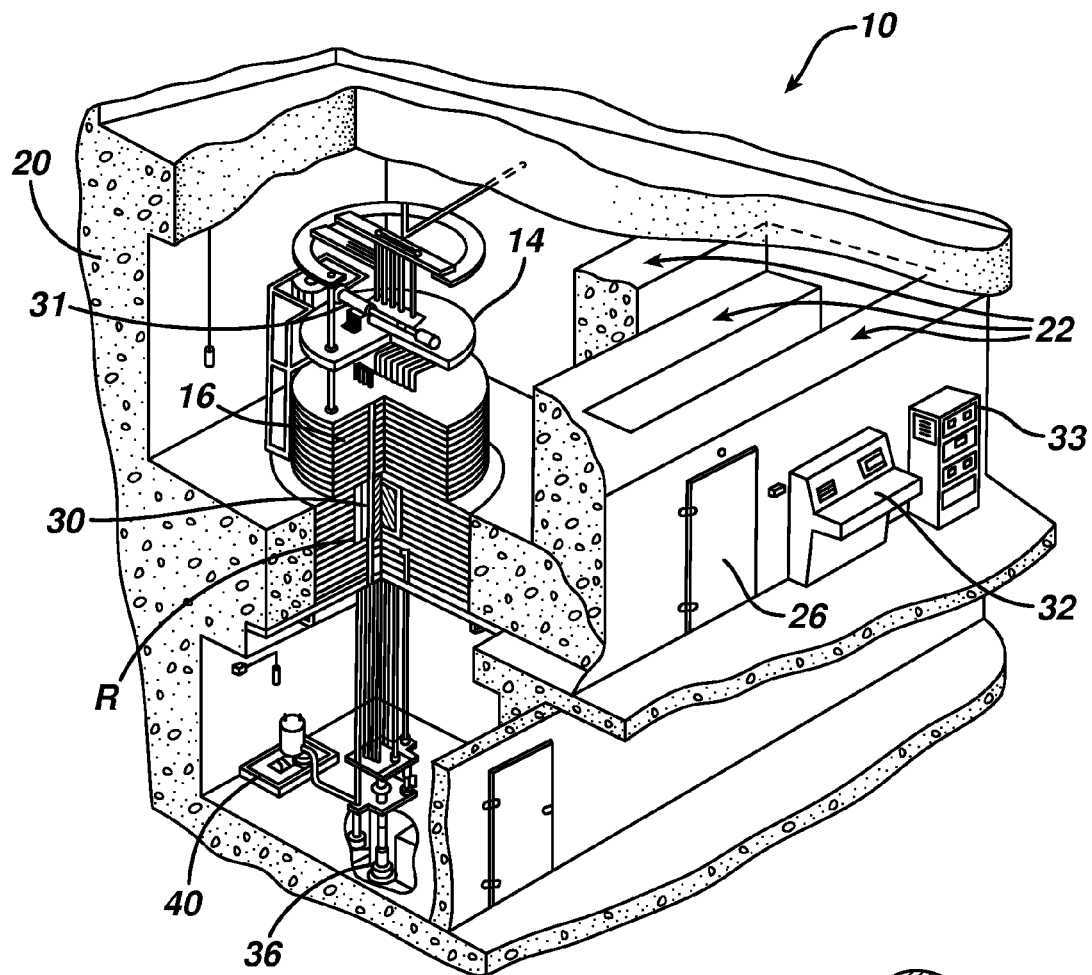
FIG. 3 is a perspective, cut-away view of a gamma irradiator housed in a concrete vault.
Figure 4:
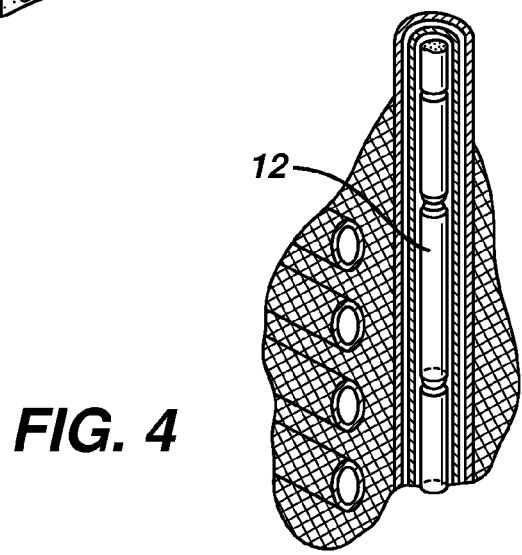
FIG. 4 is an enlarged perspective view of region R of FIG. 3.

Referring to FIGS. 3 and 4 (an enlarged view of region R), gamma radiation can be provided by a gamma irradiator 10 that includes gamma radiation sources 408, e.g., $^{60}$Co pellets, a working table 14 for holding the materials to be irradiated, and storage 16, e.g., made of a plurality iron plates. All of these components are housed in a concrete containment chamber (vault) 20 that includes a maze entranceway 22 beyond a lead-lined door 26. Storage 16 defines a plurality of channels 30, e.g., sixteen or more channels, allowing the gamma radiation sources to pass through storage on their way proximate the working table.

In operation, the sample to be irradiated is placed on a working table. The irradiator is configured to deliver the desired dose rate and monitoring equipment is connected to an experimental block 31. The operator then leaves the containment chamber, passing through the maze entranceway and through the lead-lined door. The operator mans a control panel 32, instructing a computer 33 to lift the radiation sources 12 into working position using cylinder 36 attached to hydraulic pump 40.

Gamma radiation has the advantage of significant penetration depth. Sources of gamma rays include radioactive nuclei, such as isotopes of cobalt, calcium, technicium, chromium, gallium, indium, iodine, iron, krypton, samarium, selenium, sodium, thalium and xenon.

Sources of x-rays include electron beam collision with metal targets, such as tungsten or molybdenum or alloys, or compact light sources, such as those produced commercially by Lyncean Technologies, Inc., of Palo Alto, Calif.

Sources for ultraviolet radiation include deuterium or cadmium lamps.

Sources for infrared radiation include sapphire, zinc or selenide window ceramic lamps.

Sources for microwaves include klystrons, Slevin type RF sources or atom beam sources that employ hydrogen, oxygen or nitrogen gases.

In some embodiments, a beam of electrons is used as the radiation source. A beam of electrons has the advantages of high dose rates (e.g., 1, 5, or even 10 MRad per second), high throughput, less containment and less confinement equipment. Electrons can also be more efficient at causing chain scission. In addition, electrons having energies of 4-10 MeV can have penetration depths of 5 to 30 mm or more, such as 40 mm.

Electron beams can be generated, e.g., by electrostatic generators, cascade generators, transformer generators, low energy accelerators with a scanning system, low energy accelerators with a linear cathode, linear accelerators, and pulsed accelerators. Electrons as an ionizing radiation source can be useful, e.g., for relatively thin materials, e.g., less than 0.5 inch, e.g., less than 0.4 inch, 0.3 inch, 0.2 inch, or less than 0.1 inch. In some embodiments, the energy of each electron of the electron beam is from about 0.25 MeV to about 7.5 MeV (million electron volts), e.g., from about 0.5 MeV to about 5.0 MeV, or from about 0.7 MeV to about 2.0 MeV. Electron beam irradiation devices may be procured commercially from Ion Beam Applications, Louvain-la-Neuve, Belgium or from Titan Corporation, San Diego, CA. Typical electron energies can be 1, 2, 4.5, 7.5, or 10 MeV. Typical electron beam irradiation device power can be 1, 5, 10, 20, 50, 100, 250, or 500 kW. Typical doses may take values of 1, 5, 10, 20, 50, 100, or 200 kGy.

Tradeoffs in considering electron beam irradiation device power specifications include operating costs, capital costs, depreciation and device footprint. Tradeoffs in considering exposure dose levels of electron beam irradiation would be energy costs and environment, safety, and health (ESH) concerns. Generators are typically housed in a vault, e.g., of lead or concrete.

The electron beam irradiation device can produce either a fixed beam or a scanning beam. A scanning beam may be advantageous with large scan sweep length and high scan speeds, as this would effectively replace a large, fixed beam width. Further, available sweep widths of 0.5 m, 1 m, 2 m or more are available.

In embodiments in which the irradiating is performed with electromagnetic radiation, the electromagnetic radiation can have an energy per photon (in electron volts) of, e.g., greater than $10^2$ eV, e.g., greater than $10^3$, $10^4$, $10^5$, $10^6$ or even greater than $10^7$ eV. In some embodiments, the electromagnetic radiation has energy per photon of between $10^4$ and $10^7$, e.g., between $10^5$ and $10^6$ eV. The electromagnetic radiation can have a frequency of, e.g., greater than $10^{16}$ hz, greater than $10^{17}$ hz, $10^{18}$, $10^{19}$, $10^{20}$ or even greater than $10^{21}$ hz. In some embodiments, the electromagnetic radiation has a frequency of between $10^{18}$ and $10^{22}$ hz, e.g., between $10^{19}$ to $10^{21}$ hz.

Figure 5:
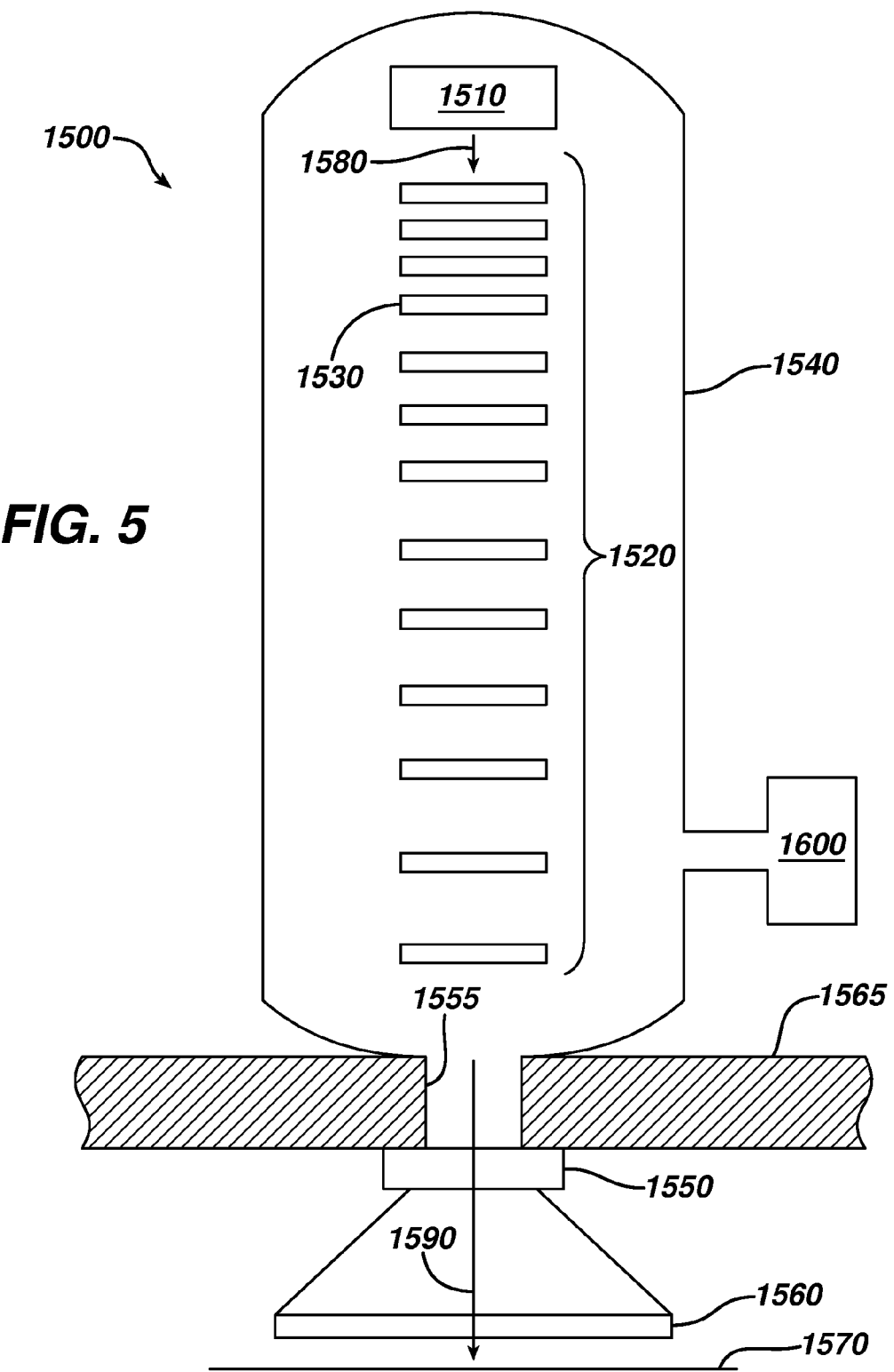
FIG. 5 is a schematic diagram of a DC accelerator.

One type of accelerator that can be used to accelerate ions produced using the sources discussed above is a Dynamitron® (available, for example, from Radiation Dynamics Inc., now a unit of IBA, Louvain-la-Neuve, Belgium). A schematic diagram of a Dynamitron® accelerator 1500 is shown in FIG. 5. Accelerator 1500 includes an injector 1510 (which includes an ion source) and an accelerating column 1520 that includes a plurality of annular electrodes 1530. Injector 1510 and column 1520 are housed within an enclosure 1540 that is evacuated by a vacuum pump 1600.

Injector 1510 produces a beam of ions 1580, and introduces beam 1580 into accelerating column 1520. The annular electrodes 1530 are maintained at different electric potentials, so that ions are accelerated as they pass through gaps between the electrodes (e.g., the ions are accelerated in the gaps, but not within the electrodes, where the electric potentials are uniform). As the ions travel from the top of column 1520 toward the bottom in FIG. 5, the average speed of the ions increases. The spacing between subsequent annular electrodes 1530 typically increases, therefore, to accommodate the higher average ion speed.

After the accelerated ions have traversed the length of column 1520, the accelerated ion beam 1590 is coupled out of enclosure 1540 through delivery tube 1555. The length of delivery tube 1555 is selected to permit adequate shielding (e.g., concrete shielding) to be positioned adjacent to column 1520, isolating the column. After passing through tube 1555, ion beam 1590 passes through scan magnet 1550. Scan magnet 1550, which is controlled by an external logic unit (not shown), can sweep accelerated ion beam 1590 in controlled fashion across a two-dimensional plane oriented perpendicular to a central axis of column 1520. As shown in FIG. 5, ion beam 1590 passes through window 1560 (e.g., a metal foil window or screen) and then is directed to impinge on selected regions of a sample 1570 by scan magnet 1550.

In some embodiments, the electric potentials applied to electrodes 1530 are static potentials, generated, e.g., by DC potential sources. In certain embodiments, some or all of the electric potentials applied to electrodes 1530 are variable potentials generated by variable potential sources. Suitable variable sources of large electric potentials include amplified field sources, e.g. such as klystrons. Accordingly, depending upon the nature of the potentials applied to electrodes 1530, accelerator 1500 can operate in either pulsed or continuous mode.

To achieve a selected accelerated ion energy at the output end of column 1520, the length of column 1520 and the potentials applied to electrodes 1530 are chosen based on considerations well-known in the art. However, it is notable that to reduce the length of column 1520, multiply-charged ions can be used in place of singly-charged ions. That is, the accelerating effect of a selected electric potential difference between two electrodes is greater for an ion bearing a charge of magnitude 2 or more than for an ion bearing a charge of magnitude 1. Thus, an arbitrary ion $X^{2+}$ can be accelerated to final energy E over a shorter length than a corresponding arbitrary ion $X^{3\circ}$. Triply- and quadruply-charged ions (e.g., $X^{3+}$ and $X^{4+}$) can be accelerated to final energy E over even shorter distances. Therefore, the length of column 1520 can be significantly reduced when ion beam 1580 includes primarily multiply-charged ion species.

To accelerate positively-charged ions, the potential differences between electrodes 1530 of column 1520 are selected so that the direction of increasing field strength in FIG. 5 is downward (e.g., toward the bottom of column 1520). Conversely, when accelerator 1500 is used to accelerate negatively-charged ions, the electric potential differences between electrodes 1530 are reversed in column 1520, and the direction of increasing field strength in FIG. 5 is upward (e.g., toward the top of column 1520). Reconfiguring the electric potentials applied to electrodes 1530 is a straightforward procedure, so that accelerator 1500 can be converted relatively rapidly from accelerating positive ions to accelerating negative ions, or vice versa. Similarly, accelerator 1500 can be converted rapidly from accelerating singly-charged ions to accelerating multiply-charged ions, and vice versa.

Various methods may be used for the generation of ions suitable for ion beams which may be used in treating the paper or the starting cellulosic or lignocellulosic materials. After the ions have been generated, they are typically accelerated in one or more of various types of accelerators, and then directed to impinge on the material to be treated. Various types of accelerators and ion beam generating equipment are described in U.S. Ser. No. 12/417,707, incorporated by reference hereinabove.

Doses

In some embodiments, irradiating (with any radiation source or a combination of sources) is performed until the material receives a dose of at least 0.05 MRad, e.g., at least 0.1, 0.25, 1.0, 2.5, or 5.0 MRad. In some embodiments, irradiating is performed until the material receives a dose of between 0.1 and 2.5 MRad. Other suitable ranges include between 0.25 MRad and 4.0 MRad, between 0.5 MRad and 3.0 MRad, and between 1.0 MRad and 2.5 MRad.

The degree of functionalization achieved is generally higher the higher the dose.

In some embodiments, the irradiating is performed at a dose rate of between 5.0 and 1500.0 kilorads/hour, e.g., between 10.0 and 750.0 kilorads/hour or between 50.0 and 350.0 kilorads/hours. When high throughput is desired, e.g., in a high speed papermaking process, radiation can be applied at, e.g., 0.5 to 3.0 MRad/sec, or even faster, using cooling to avoid overheating the irradiated material.

In some embodiments in which coated paper is irradiated, the paper coating includes resin that is cross-linkable, e.g., diacrylate or polyethylene. In some cases, the resin crosslinks as the paper is irradiated, which can provide a synergistic effect to optimize the scuff resistance and other surface properties of the paper. In these embodiments, the dose of radiation is selected to be sufficiently high so as to achieve the desired functionalization of the paper, i.e., at least about 0.25 to about 2.5 MRad, depending on the material, while being sufficiently low so as to avoid deleteriously affecting the paper coating. The upper limit on the dose will vary depending on the composition of the coating, but in some embodiments the preferred dose is less than about 5 MRad.

In some embodiments, two or more radiation sources are used, such as two or more ionizing radiations. For example, samples can be treated, in any order, with a beam of electrons, followed by gamma radiation and/or UV light having wavelengths from about 100 nm to about 280 nm. In some embodiments, samples are treated with three ionizing radiation sources, such as a beam of electrons, gamma radiation, and energetic UV light.

Identifying Marked Paper Products

Paper products that have been marked using the methods described herein are distinguishable from similar looking unmarked paper products by determining the functionality of the paper. This can be accomplished, for example, by preparing an IR scan of the paper in question, using an infrared spectrometer, and comparing the scan to a "control" IR scan of a marked paper. For example, if the marked paper has been by functionalized so as to increase the number of carboxylic acid groups in the paper, the IR scan of a paper being tested to see whether it has been similarly marked should have a carboxyl peak that is substantially the same height as the carboxyl peak in the control IR scan.

Alternative methods of testing whether a paper has been marked or not include AFM, CFM, and ESR.

Paper Additives

Any of the many additives and coatings used in the papermaking industry can be added to or applied to the fibrous materials, papers, or any other materials and products described herein. Additives include fillers such as calcium carbonate, plastic pigments, graphite, wollastonite, mica, glass, fiber glass, silica, and talc; inorganic flame retardants such as alumina trihydrate or magnesium hydroxide; organic flame retardants such as chlorinated or brominated organic compounds; carbon fibers; and metal fibers or powders (e.g., aluminum, stainless steel). These additives can reinforce, extend, or change electrical or mechanical properties, compatibility properties, or other properties. Other additives include starch, lignin, fragrances, coupling agents, antioxidants, opacifiers, heat stabilizers, colorants such as dyes and pigments, polymers, e.g., degradable polymers, photostabilizers, and biocides. Representative degradable polymers include polyhydroxy acids, e.g., polylactides, polyglycolides and copolymers of lactic acid and glycolic acid, poly(hydroxybutyric acid), poly(hydroxyvaleric acid), poly[lactide-co-(e-caprolactone)], poly[glycolide-co-(e-caprolactone)], polycarbonates, poly(amino acids), poly(hydroxyalkanoate)s, polyanhydrides, polyorthoesters and blends of these polymers.

If desired, various cross-linking additives can be added. Such additives include materials that are cross-linkable themselves and materials that will assist with cross-linking of the cellulosic or lignocellulosic material in the paper. Cross-linking additives include, but are not limited to, lignin, starch, diacrylates, divinyl compounds, and polyethylene. In some implementations, such additives are included in concentrations of about 0.25% to about 2.5%, e.g., about 0.5% to about 1.0%.

When additives are included, they can be present in amounts, calculated on a dry weight basis, of from below about 1 percent to as high as about 80 percent, based on total weight of the fibrous material. More typically, amounts range from between about 0.5 percent to about 50 percent by weight, e.g., from about 0.5 percent to about 5 percent, 10 percent, 20 percent, 30, percent or more, e.g., 40 percent.

Any additives described herein can be encapsulated, e.g., spray dried or microencapsulated, e.g., to protect the additives from heat or moisture during handling.

Suitable coatings include any of the many coatings used in the paper industry to provide specific surface characteristics, including performance characteristics required for particular printing applications.

As mentioned above, various fillers can be included in the paper. For example, inorganic fillers such as calcium carbonate (e.g., precipitated calcium carbonate or natural calcium carbonate), aragonite clay, orthorhombic clays, calcite clay, rhombohedral clays, kaolin clay, bentonite clay, dicalcium phosphate, tricalcium phosphate, calcium pyrophosphate, insoluble sodium metaphosphate, precipitated calcium carbonate, magnesium orthophosphate, trimagnesium phosphate, hydroxyapatites, synthetic apatites, alumina, silica xerogel, metal aluminosilicate complexes, sodium aluminum silicates, zirconium silicate, silicon dioxide or combinations of the inorganic additives may be used. The fillers can have, e.g., a particle size of greater than 1 micron, e.g., greater than 2, 5, 10, or 25 microns or even greater than 35 microns.

Nanometer scale fillers can also be used alone, or in combination with fibrous materials of any size and/or shape. The fillers can be in the form of, e.g., particles, plates or fibers. For example, nanometer sized clays, silicon and carbon nanotubes, and silicon and carbon nanowires can be used. The fillers can have a transverse dimension less than 1000 nm, e.g., less than 900, 800, 750, 600, 500, 350, 300, 250, 200, or 100 nm, or even less than 50 nm.

In some embodiments, the nano-clay is a montmorillonite. Such clays are available from Nanocor, Inc. and Southern Clay products, and have been described in U.S. Pat. Nos. 6,849,680 and 6,737,464. The clays can be surface treated before mixing into, e.g., a resin or a fibrous material. For example, the clay can be surface treated so that its surface is ionic in nature, e.g., cationic or anionic.

Aggregated or agglomerated nanometer scale fillers, or nanometer scale fillers that are assembled into supramolecular structures, e.g., self-assembled supramolecular structures can also be used. The aggregated or supramolecular fillers can be open or closed in structure, and can have a variety of shapes, e.g., cage, tube or spherical.

Lignin Content

The paper products discussed herein can contain lignin, for example up to 1, 2, 3, 4, 5, 7.5, 10, 15, 20, or even 25% by weight of lignin. This lignin content can be the result of the lignin present in the lignocellulosic material(s) used to manufacture the paper. Alternatively, or in addition, lignin can be added to the paper as an additive, as mentioned above. In this case, the lignin can be added as a solid, e.g., as a powder or other particulate material, or can be dissolved or dispersed and added in liquid form. In the latter case, the lignin can be dissolved in solvent or a solvent system. The solvent or solvent system can be in the form of a single phase or two or more phases. Solvent systems for cellulosic and lignocellulosic materials include DMSO-salt systems. Such systems include, for example, DMSO in combination with a lithium, magnesium, potassium, sodium or zinc salt. Lithium salts include LiCl, LiBr, LiI, lithium perchlorate and lithium nitrate. Magnesium salts include magnesium nitrate and magnesium chloride. Potassium salts include potassium iodide and nitrate. Examples of sodium salts include sodium iodide and nitrate. Examples of zinc salts include zinc chloride and nitrate. Any salt can be anhydrous or hydrated. Typical loadings of the salt in the DMSO are between about 1 and about 50 percent, e.g., between about 2 and 25, between about 3 and 15 or between about 4 and 12.5 percent by weight.

In some cases, lignin will cross-link in the paper during irradiation, further enhancing the physical properties of the paper.

Paper Types

Paper is often characterized by weight. The weight assigned to a paper is the weight of a ream, 500 sheets, of varying "basic sizes," before the paper is cut into the size as sold to end customers. For example, a ream of 20 lb, 8½×11" paper weighs 5 pounds, because it has been cut from a larger sheet into four pieces. In the United States, printing paper is generally 20 lb, 24 lb, or 32 lb at most. Cover stock is generally 68 lb, and 110 lb or more.

In Europe the weight is expressed in grams per square meter (gsm or just g). Printing paper is generally between 60 g and 120 g. Anything heavier than 160 g is considered card stock. The weight of a ream therefore depends on the dimensions of the paper, e.g., one ream of A4 (210 mm×297 mm) size (approx 8.27"×11.7") weighs 2.5 kilograms (approx 5.5 pounds).

The density of paper ranges from 250 kg/m$^3$ (16 lb/ft$^3$) for tissue paper to 1500 kg/m3 (94 lb/ft$^3$) for some specialty paper. In some cases the density of printing paper is about 800 kg/m$^3$ (50 lb/ft$^3$).

The processes described herein are suitable for use with all of these grades of paper, as well as other types of paper such as corrugated cardboard, paper board, and other paper products. The processes described herein may be used to treat paper that is used, for example, in any of the following applications: as postage stamps; as paper money, bank notes, securities, checks, and the like; in books, magazines, newspapers, and art; and for packaging, e.g., paper board, corrugated cardboard, paper bags, envelopes, and boxes. The paper may be single-layer or multi-layer paper, or may form part of a laminate. The marking can be used in commerce to indicate purchase, use, or other events. For example, marking can be used to "cancel" postage, or to indicate where and/or when an item was purchased.

The paper may be made of any desired type of fiber, including fiber derived from wood and recycled paper, as well as fiber derived from other sources. Vegetable fiber materials, such as cotton, hemp, linen, and rice, can be used alone or in combination with each other or with wood-derived fibers. Other non-wood fiber sources include, but are not limited to, sugarcane, bagasse, straw, bamboo, kenaf, jute, flax, and cotton. A wide variety of synthetic fibers, such as polypropylene and polyethylene, as well as other ingredients such as inorganic fillers, may be incorporated into paper as a means for imparting desirable physical properties. It may be desirable to include these non-wood fibers in paper used in special application such as for paper money, fine stationary, art paper and other applications requiring particular strength or aesthetic characteristics.

The paper may be irradiated before or after printing.

Process Water

In the processes disclosed herein, whenever water is used in any process, it may be grey water, e.g., municipal grey water, or black water. In some embodiments, the grey or black water is sterilized prior to use. Sterilization may be accomplished by any desired technique, for example by irradiation, steam, or chemical sterilization.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of identifying whether a paper product is marked, the method comprising
   comparing the functionalization of a sample paper product to the functionalization of a marked paper product,
   the functionalization of the marked paper product having been altered by irradiating the paper product with accelerated electrons or accelerated particles heavier than an electron, wherein the paper product is irradiated with a total dosage of at least 0.1 Mrad and the electrons or particles have an energy of at least 0.25 MeV.

2. The method of claim 1 wherein comparing comprises determining the functionalization of the sample paper product using a technique selected from the group consisting of AFM, CFM, ESR and IR.

3. The method of claim 1 wherein comparing comprises comparing the number of carboxylic acid groups present in the sample paper product with the number of carboxylic acid groups present in the marked paper product.

4. The method of claim 1 wherein comparing comprises determining whether the sample paper product includes a region of altered functionalization that resembles a region of altered functionalization on the marked paper product.

5. The method of claim 4 wherein the region of altered functionalization on the marked paper product defines a symbol.

6. The method of claim 5 wherein the paper product comprises paper money.

7. The method of claim 6 wherein the symbol comprises a watermark.

8. The method of claim 7 wherein the sample is suspected to be counterfeit money.

9. The method of claim 1 wherein the paper product comprises a note.

10. The method of claim 1 wherein the paper product comprises currency.

11. The method of claim 1 wherein irradiation has been performed with an electron beam.

\* \* \* \* \*